United States Patent
Juozaitis

[11] Patent Number: 6,047,403
[45] Date of Patent: Apr. 11, 2000

[54] DECORATIVE CAST COVERING

[76] Inventor: Penny Juozaitis, 1522 Forest Ave., River Forest, Ill. 60305

[21] Appl. No.: 09/189,430

[22] Filed: Nov. 12, 1998

[51] Int. Cl.[7] .............................. A41D 27/12; A41B 11/00
[52] U.S. Cl. .......................................... 2/61; 2/239; 2/242
[58] Field of Search ............................ 2/22, 23, 61, 239, 2/241, 242; 602/62, 63; 36/7.2, 8.1, 110, 7.1 R

[56] References Cited

U.S. PATENT DOCUMENTS

| | | | |
|---|---|---|---|
| 615,271 | 12/1898 | Hayden et al. | |
| 1,044,567 | 11/1912 | Parsons | |
| 2,244,871 | 6/1941 | Guinzburg | |
| 3,416,518 | 12/1968 | Samuels et al. | |
| 3,497,875 | 3/1970 | Rivera | |
| 3,605,122 | 9/1971 | Myers | |
| 3,735,758 | 5/1973 | Novotney | 602/3 |
| 3,735,759 | 5/1973 | MacKay | 602/3 |
| 3,747,125 | 7/1973 | Goldman et al. | 2/240 |
| 4,069,515 | 1/1978 | Swallow et al. | 2/239 |
| 4,599,812 | 7/1986 | Harmsen | 36/1.5 |
| 4,639,945 | 2/1987 | Betz | 2/22 |
| 4,722,143 | 2/1988 | Everett | 36/7.1 R |
| 4,961,235 | 10/1990 | Williger | 2/239 |
| 5,063,919 | 11/1991 | Silverberg | 602/3 |
| 5,412,957 | 5/1995 | Bradberry et al. | 66/178 A |
| 5,625,904 | 5/1997 | Kline | 2/239 |
| 5,664,263 | 9/1997 | Reynolds | 2/239 |

*Primary Examiner*—John J. Calvert
*Assistant Examiner*—Shirra L. Jenkins
*Attorney, Agent, or Firm*—Wallenstein & Wagner, Ltd.

[57] ABSTRACT

A decorative cast covering for a full leg cast, comprising an elongated, generally cylindrical sleeve having an upper end and a lower end; and a first elastomeric band fixed to the cast covering adjacent the lower end. In this way, the lower end can be securely fastened by the elastomeric band to the bottom of the leg cast. The decorative cast covering further comprises a pocket secured along the generally cylindrical sleeve.

14 Claims, 1 Drawing Sheet

DECORATIVE CAST COVERING

TECHNICAL FIELD

This invention is directed to a decorative covering for a plaster or other cast that immobilizes human bones, especially arms and legs, when they have been broken.

BACKGROUND OF THE INVENTION

Casts of plaster or other materials are used to immobilize bones, especially arm or leg bones, that have been broken and that must be immobilized for several weeks so that the bone will heal properly. Invariably, people will attempt to decorate or write upon these casts. In addition, various types of cast coverings are known in the art.

For example, U.S. Pat. No. 5,720,712 is directed to a re-useable limb protector for use with a cast or bandage. The limb protector includes a stretchable, moisture-impervious material that is adjustable in size to accommodate a wide range of individuals, and is molded of a single piece of skid retardant material. It has a water-tight seal that is accomplished by stretching the moisture impervious base unit, and is locked in place by the folding over of two locking straps. As can be seen by FIG. 1 of this patent, the limb protector ends well above the lowermost point of the cast, approximately at the ankle, and thus does not cover the foot portion of the cast, or the exposed toes of the individual wearing the cast.

U.S. Pat. No. 4,911,151 is directed to a waterproof covering for a cast or bandage. The cast covering of this patent has only one open end. The open end includes a flexible plastic strap which secures the covering to the arm or leg of the user at a point above the cast.

U.S. Pat. No. 4,646,727 discloses a leg cast covering, including a foot sock complemented by a leg sock having a heel portion and a foot opening adjoining the heel portion. Although this two-piece covering includes a provision for covering a portion of the foot, it does not cover either the toes, nor the toe portion of the leg cast.

U.S. Pat. No. 3,329,143 discloses a shrinkable plastic bandage cover. As may be seen in FIG. 2 of this patent, the invention relates to a plastic bandage cover which is shrinkable into place over a cast or bandage by heating that cover. As the cover cools, it contracts and shrinks into a tight fit over the cast or bandage. Again, as can be seen in each of FIGS. 1–5 of this patent, the cast or bandage cover does not extend to cover the toes or fingers of the user.

U.S. Pat. No. 5,581,817 is of minor interest, as it is not related to a cast covering. Rather, this patent is directed to a sports sock which can be folded over to contain a shin guard. See especially FIGS. 1 and 2.

U.S. Pat. No. 5,005,215 is similarly of relatively minor interest, as it is directed to a chap that encircles the leg, not the cast, of a user to protect that user from ticks, other arachnids, and crawling insects.

U.S. Pat. No. 4,951,317 is similarly directed to an article for an arm or leg, not for covering a cast. This article of clothing is worn by athletes to protect their arm muscles, or lower leg muscles, from the damaging effects of cold air or cold wind.

U.S. Pat. No. 4,306,315 is directed to a shin guard comprising an elastic, generally tubular member adapted to tightly surround the lower leg of a wearer in the vicinity of the shin. As may be seen in FIG. 3, this shin guard extends to a position above the ankle of the wearer, and does not cover the toes of the wearer. A stirrup 12 retains the shin guard on the leg of the wearer.

SUMMARY OF THE INVENTION

The invention is a decorative cast covering for a full leg or arm cast. The decorative covering comprises an elongated, generally cylindrical sleeve having an upper end and a lower end. A first elastomeric band is fixed to the cast covering adjacent the lower end so that the lower end can be securely fastened by the first elastomeric band to the bottom of the leg cast.

The decorative cast covering further comprises a pocket secured along the generally cylindrical sleeve. Preferably, a hook and loop type fastener is secured near the top of the pocket for closing the pocket.

The decorative cast covering further comprises a second elastomeric band adjacent the upper end of the generally cylindrical sleeve. It may also comprise a third elastomeric band between the first and second elastomeric bands.

Preferably, the cylindrical sleeve of the decorative cast covering is made of a textile fabric. A preferred textile fabric is a velvet fabric.

DETAILED DESCRIPTION OF THE PREFERRED EMBODIMENT OF THE INVENTION

While this invention is susceptible of embodiment in many different forms, the drawings and specification describe in detail preferred embodiments of the invention. It should be understood, however, that the disclosure is to be considered as an exemplification of the principles of the invention. The disclosure is not intended to limit the broadest aspects of the invention to the illustrated embodiments.

The invention is a decorative cast covering 10 for a full leg cast or an arm cast. Although the FIGURES show only the use of the decorative cast covering 10 on a full leg cast 20, it is clear that the invention can be equally effective as a covering for an arm cast.

The decorative covering 10 is essentially an elongated, generally cylindrical sleeve 12. However, it is clear that the sleeve 12 need not be of a cylindrical shape, but can be any of a number of other shapes. The sleeve is, however, preferably made of a non-rigid or flexible substance.

Figure 2:
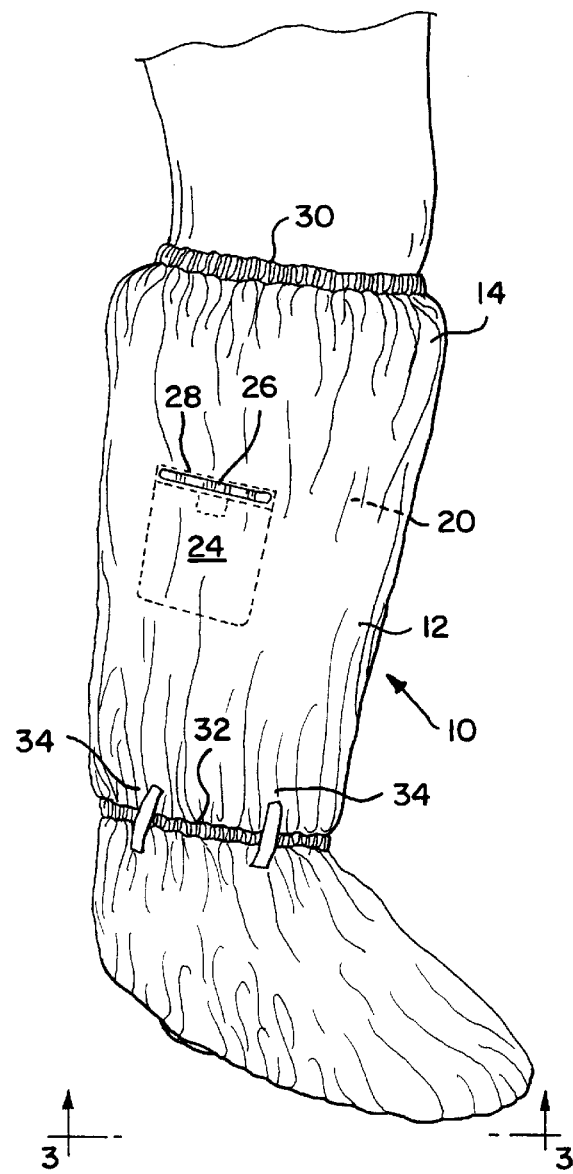
FIG. 2 is a perspective view of the cast covering of FIG. 1, but with the cast covering in place on the leg cast of a human wearer.

The sleeve 12 has an upper end 14 and a lower end 16. The upper end 14, as may be seen in FIG. 2, is generally secured near the knee of the wearer of the cast 20. As may be seen from a review of FIG. 3, a first elastomeric band 18 is secured to the cast covering 10 adjacent the lower end 16 of the sleeve 12. In this way, the lower end 16 can be securely fastened by the first elastomeric band 18 to the leg cast 20, particularly at the bottom 22 of the leg cast 20. As a result of this particular configuration shown in FIG. 3, where the first elastomeric band 18 abuts against the bottom 22 of the cast 20, the decorative cast covering 10 covers the entire generally visible portion of the cast 20 (FIG. 2). Yet, as may be seen in FIG. 3, only a portion of the bottom of the cast 20 is covered by the decorative covering 10. As a result, as may also be seen in FIG. 3, a part of the bottom 22 of the cast 20 remains exposed. This configuration prevents excessive wear of the cast covering 10, especially the lower end 16 of the cast covering 10 near the lower end of the sleeve 12.

The decorative cast covering 10 further comprises a pocket 24 secured to or along the generally cylindrical sleeve 12. The pocket 24 can be of any convenient size, and enables one to carry articles that would otherwise be carried in pockets of the wearer's clothing, or in the purse of a wearer.

Persons wearing a heavy leg cast have, by definition, a more limited ability to move about or otherwise maneuver. To prevent the inadvertent loss of items in this pocket 24, and to minimize the necessity of retrieving items that have dropped out of the pocket 24, a hook and loop type fastener 26 is secured near the top 28 of the pocket 24 for closing the pocket 24. As is conventional, the hook portion of the fastener 26 is pushed together with the loop portion of the fastener 26 to close the top of the pocket 24. Similarly, the hook portion of the fastener 26 is pulled apart from the loop portion of the fastener 26 to open the top of the pocket 24.

The decorative cast covering 10 further comprises a second elastomeric band 30 adjacent the upper end 14 of the generally cylindrical sleeve 12. This band 30 secures the upper end 14 of the generally cylindrical sleeve 12 to a point near the knee of the wearer.

A third elastomeric band 32 is secured to the decorative cast covering 10 at a point between the first elastomeric band 18 and the second elastomeric band 30. This third elastomeric band 32 secures the cast covering 10 at a point near the ankle of the wearer.

Figure 1:
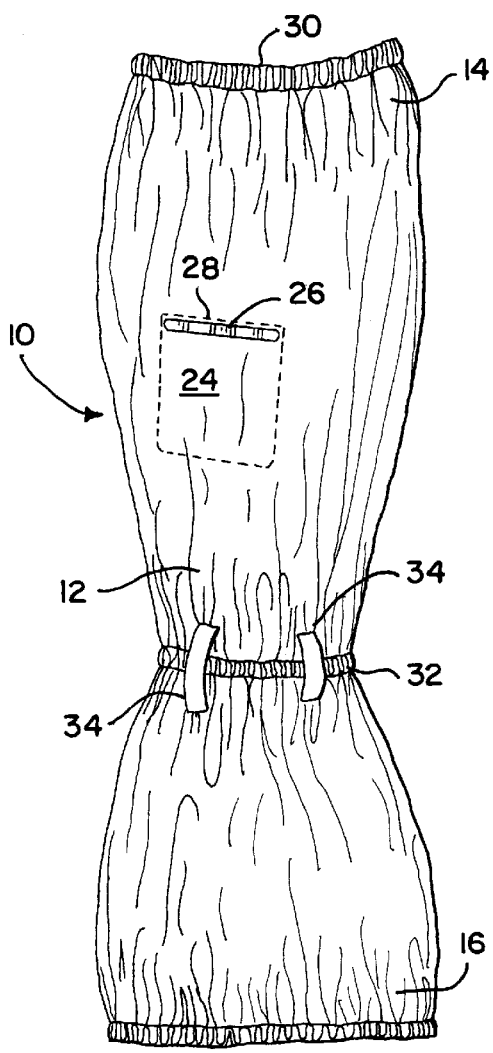
FIG. 1 is a perspective view of the invention, showing a perspective view of the decorative cast covering in accordance with the invention, and showing a pocket with a hook and loop type fastener which acts as a closure for the top of the pocket.

Preferably, the cylindrical sleeve 12 of the decorative cast covering 10 is made of a textile fabric. A preferred textile fabric, as depicted in FIGS. 1–3, is a velvet fabric.

Figure 3:
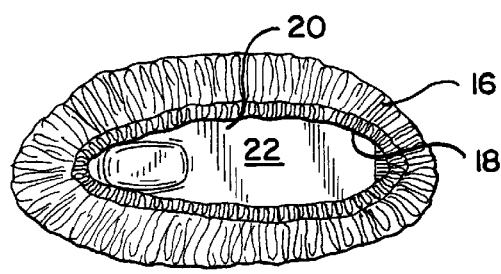
FIG. 3 is a view along lines 3—3 of FIG. 2, showing the decorative cast covering in place, and particularly showing its securement to the bottom of the cast.

As may be seen in FIG. 3, the cast covering 10 may also include one or more loops 34. Three to four of such loops 34 are generally sufficient for the purposes of this invention. These loops 34 are somewhat similar, in structure and function, to the belt loops on men's trousers. Particularly, these loops 34 may be used to support a decorative, colored sash or band (not shown) to further add to the decorative nature of this cast covering 10.

Specific embodiments have been illustrated and described. Numerous modifications are possible, which modifications do not significantly depart from the spirit of the invention. Protection is only limited by the scope of the accompanying claims.

What I claim is:

1. A decorative cast covering for a full leg cast that covers the entire generally visible portion of said cast, said decorative covering comprising an elongated sleeve having an upper end and a lower end; and a first elastomeric band fixed to said cast covering adjacent said lower end so that said lower end can be securely fastened by said elastomeric band to the bottom of said leg cast, wherein only a portion of the bottom of the cast is covered by said decorative cast covering.

2. The decorative cast covering of claim 1, further comprising a pocket secured along said sleeve.

3. The decorative cast covering of claim 2, further comprising a hook and loop type fastener secured near the top of said pocket for closing said pocket.

4. The decorative cast covering of claim 1, further comprising a second elastomeric band adjacent said upper end of said sleeve.

5. The decorative cast covering of claim 4, further comprising a third elastomeric band between said first and second elastomeric bands.

6. The decorative cast covering of claim 1, wherein said sleeve is made of a textile fabric.

7. The decorative cast covering of claim 6, wherein said sleeve is made of a velvet fabric.

8. A decorative cast covering for a full leg cast that covers the entire generally visible portion of said cast, said decorative covering comprising an elongated, generally cylindrical sleeve having an upper end and a lower end; and a first elastomeric band fixed to said cast covering adjacent said lower end so that said lower end can be securely fastened by said elastomeric band to the bottom of said leg cast, and further comprising a pocket secured along said generally cylindrical sleeve, wherein only a portion of the bottom of the cast is covered by said decorative cast covering.

9. The decorative cast covering of claim 8, further comprising a hook and loop type fastener secured near the top of said pocket for closing said pocket.

10. The decorative cast covering of claim 8, further comprising a second elastomeric band adjacent said upper end of said generally cylindrical sleeve.

11. The decorative cast covering of claim 10, further comprising a third elastomeric band between said first and second elastomeric bands.

12. The decorative cast covering of claim 8, wherein said cylindrical sleeve is made of a textile fabric.

13. The decorative cast covering of claim 12, wherein said cylindrical sleeve is made of a velvet fabric.

14. The decorative cast covering of claim 8, further comprising one or more loops.

\* \* \* \* \*